United States Patent
Hoermansdoerfer

[11] Patent Number: 6,146,425
[45] Date of Patent: Nov. 14, 2000

[54] HIP JOINT GLENOID CAVITY WITH A SPECIAL THREAD

[76] Inventor: Gerd Hoermansdoerfer, Ot Beinhorn, Kastanieneck 6A, 31303 Burgdorf, Germany

[21] Appl. No.: 09/171,506
[22] PCT Filed: Apr. 21, 1997
[86] PCT No.: PCT/DE97/00793
§ 371 Date: Oct. 21, 1998
§ 102(e) Date: Oct. 21, 1998
[87] PCT Pub. No.: WO97/39702
PCT Pub. Date: Oct. 30, 1997

[30] Foreign Application Priority Data

Apr. 22, 1996 [DE] Germany ............... 196 15 876

[51] Int. Cl.[7] .................................................. A61F 2/32
[52] U.S. Cl. ............................................... 623/22.31
[58] Field of Search ................ 623/22, 23, 22.31, 623/22.32, 23.11, 23.12, 23.13, 23.14, 22.27, 22.21–22.39

[56] References Cited

U.S. PATENT DOCUMENTS

| | | | |
|---|---|---|---|
| 4,834,759 | 5/1989 | Spotorno et al. | 623/22 |
| 4,919,677 | 4/1990 | Stuhmer et al. | 623/22 |
| 4,963,154 | 10/1990 | Anapliotis et al. | 623/22 |
| 5,358,533 | 10/1994 | Noiles et al. | 623/22 |
| 5,443,520 | 8/1995 | Zweymuller et al. | 623/22 |
| 5,702,473 | 12/1997 | Albrektsson et al. | 623/22 |
| 5,755,799 | 5/1998 | Oehy et al. | 623/18 |
| 5,997,578 | 12/1999 | Hormansdorfer | 623/22 |

*Primary Examiner*—David H. Willse
*Assistant Examiner*—Suzette J. Jackson
*Attorney, Agent, or Firm*—Pendorf & Cutliff

[57] ABSTRACT

The invention concerns a screw-in type artificial hip joint socket with a special thread for implantation in human beings. Hip joint sockets of this type usually have a flat thread with parallel teeth flanks or a triangular thread with a neutral teeth position, the axial pitch being conventionally constant. However, such embodiments are unfavourable because they do not take sufficiently into account the forces which arise during implantation as well as during the intended use, or they cause an unnecessarily extensive bone bed destruction during an eventually required explantation. With the invention a purposefully optimization of the hip joint socket thread is provided, wherein the thread profile, the angular orientation of the thread teeth and a non-linear thread pitch is utilized, in order to ensure an effortless screwing, a stable seat in the long term and an unproblematic explantation (FIG. 3).

14 Claims, 3 Drawing Sheets

HIP JOINT GLENOID CAVITY WITH A SPECIAL THREAD

BACKGROUND OF THE INVENTION

The invention concerns an artificial hip joint socket with a special thread, as described in claim 1, which is intended for use as a component of an artificial joint in human beings.

DESCRIPTION OF THE RELATED ART

This type of hip joint socket with threads belongs to the class of so-called screw-in type sockets, since they are designed to be screwed into the bone matrix either after a pre-tapping with a tool or by self-tapping. In this class there are known, with respect to the shape of the outer shell, for example hypo-, hemi-, hyper- or paraspherical, conical, conic-spherical, parabolical, toroidical, elliptical and similar geometries.

With respect to the design of the threads situated upon the outer surface of the shell there exists a certain band width, for example, with regard to the thread profile of the thread ridge and the thread groove as well as to the pitch and the covered extension. In the meantime it has been realized that a subdivision of the thread profile into narrow thread ridges and broad grooves similar to a wood screw thread is advantageous, since it takes into consideration the realationship between the strength of the metallic construction material and the bone material and because the better breadth/height relationship of the bone material remaining between the thread ridges will promote the sustaining of the bone material.

In technical circles the question is still discussed, wether with respect to the shape of the thread tooth a so-called flat (or square) thread with a narrow right-angled cross-section or a slender triangular or, as the case may be, trapezoid shaped thread tooth is the better selection. The corresponding evaluation must take into consideration on the one hand the force requirement during the cutting-in process and on the other hand the short and long term fixation achievable. For both thread types it is the case, that for achieving a screwing-in process at low forces, cutting teeth with a so-called positive cutting angle must be provided along the course of the thread procession of the hip joint socket. Depending upon the number of the cutting-grooves and the therewith formed cutting teeth and the tooth geometry it can be necessary to form, behind the respective cutting tooth, a clearance angle or cut-back in order to prevent the occurrence of too strong of a jamming effect during the screwing-in process. With flat threads it is conventional, for this purpose, to cut back the circumscribing contour in the tooth head area.

The technical research has in the last few years focused above all upon the premature loosening of such hip joint sockets. The understandable goal of a problem-free useful life up to the life expectancy of the patient has been approached stepwise by optimizing the thread profile, sculpturing the thread bottom to better correspond to the contour of the shell outer surface, and coarsely texturing the outer surface. Nevertheless there still remains the need to improve such implants by appropiate fine work or tuning in such a manner that the strived-for goal is achieved. Therefor, besides a much more even transmission of forces from the implant to the acetabulum, there is in particular a demand for a noticeable reduction of the screw-in forces during implantation and a very good tactility of the position at which the outer surface of the hip joint socket comes flush against the bone matrix. With this, the risks of an insufficient deep turning-in or, as the case may be, an overturning of the implant would be easier to keep under control.

The described task is solved according to the invention by a threaded hip joint socket with the properties according to claim 1. Therewith, in a departure from the conventional screw thread having a constant progressing pitch, the pitch of the thread distributed along the outer shell surface measured in the axial direction is varied in dependence upon the curvature of the axial contour, the tooth profile, the helix angle of the cutting groove and the coarseness of the surface, said variance being based upon the cutting force distribution resulting during implantation or pre-tapping, in order to minimize the screw-in forces required. By means of an appropriate pitch variation the force requirement for screwing-in of the hip joint socket is markedly reduced und thereby the danger of a premature jamming or, as the case may be, a destruction of the pelvis is removed. Thereby the seating point of the shell outer surface of the hip joint socket against the bone bearing surface can be felt very definitely by a strong increase in torque during screwing-in, thus practically eliminating the frequent removal of the torque key and the need for optical and/or mechanical inspection. Also, in the very rare case of a possible occurrence of a socket loosening, there is, following an unscrewing of the implant, only a relatively slight furrowing of the involved bone portions to be expected, so that the bone surface can be prepared for the repeated implantation by means of a very sparing carving out.

SUMMARY OF THE INVENTION

At the same time it is proposed in accordance with the invention that the thread profile included in the above complex be tilted in the direction of the socket cap or socket pole, preferably further than usual until now, taking into consideration the load transfer from the implant to the bone matrix occuring later under conditions of use. As a result of this thread shape the load transfer conditions between the inventive implant and the bone matrix are improved as well as the rotational stability and the fixation, by reducing the load peaks occuring on one side of the thread grooves, respectively distributing the sum of static and dynamic load more evenly and over a larger surface.

Special embodiments and further developments of the invention, as well as procedures for the practical constructive realization of the thread and its pitch variation could be learned from the secondary claims.

The invention is based upon the discovery that on the three free surfaces of the thread ridge of a threaded socket, namely on the equator facing side, head end and polar facing side (in the following the positional descriptor termed "equator" is used for simplification for all geometries, even though in the strict sense it is applicable only to hemispheric shell shapes), uneven forces occur both during the actual screwing-in process during implantation as well as during the conditions of use. With the invention it is proposed that the shape and arrangement of the thread course upon the shell is designed by taking these forces into consideration and for this purpose approaching in particular a more or less flowing variation of the thread pitch.

One very simple step for employment of the invention is comprised therein, that conventional hip joint sockets which are otherwise machined with a threading of constant pitch, only in the polar side thread increase area, where the thread increases from zero height to full height, are machined with a different tooth flank pitch, in order that the forces acting upon this rising tooth profile are distributed in a calculated manner. In threaded sockets produced in a conventional manner, this thread start represents on the pole-side thread tooth flank the artifact of a ring shaped cut-out of a planar or conical surface, which results from the preliminary turning or machining. Since this portion of the surface is oriented relatively oblique with respect to the direction of screwing-in, it occurs there a higher resistance to screwing-in. By a commensurate slewing of this thread section in the polar direction the forces permit themselves to be more evenly distributed and thus minimized. For the manufacturing, which may for example involve lathe turning, it is proposed that the cutting tool for forming the polar side flank is moved along the mentioned area with a smaller pitch compared to the original thread pitch, and the equatorial flank cutting tool is moved with a larger pitch.

A significantly more advantageous embodiment of the invention is comprised therein, that the profile of the thread tooth is tilted out of the otherwise conventional neutral position in the direction towards the socket pole or, as the case may be, is tilted more than usual. In the predominant number of conventional known threaded hip joint sockets a neutral tooth orientation is preferred, that is, that the respective central axis of the thread tooth is oriented in the axial cutting plane perpendicular to the socket axis. In the conventional flat threads the two tooth flanks then accordingly run parallel and on both sides have the same distance to this middle axis, while in the threaded sockets with triangular threading the central axis thereof is represented by the bisector of the angle enclosing the two tooth flanks. In the group of the threaded sockets with triangular threads there are also known models with a profile tilted in the direction of the equator, for example, the model MECRING once produced by the company MECRON, or the model ACCU-PATH of the company HOWMEDICA. Screw-in type hip joint sockets produced with teeth tilted in the direction of the socket pole are extremely rare, among which are the model ULTIMA from the company JOHNSON & JOHNSON and MUNICH RING from the company AESCULAP. In the first of these two mentioned models the tilt angle of the central axis corresponds to not more than 4°, while in the latter the tooth profile is tilted so far that the pole-side angle corresponds to 0°. There are however no screw-in type hip joint sockets known with an axial sectional curvature of the outer shell surface and straight flank thread teeth, in which the pole-side angle of the thread profile is tilted towards the socket pole more than a value of 0°.

In the German Patent ducument DE 37 01 381 C1 a threaded hip joint socket is disclosed, where the thread teeth have a sickle shaped cross-section and where, at least with their head area, the thread teeth are tilted towards the socket pole, their tips running along an imaginary encompassing cylinder. When using this concept the entire cutting work necessary for screwing-in must be provided by only one to two cutting edges at the pole-side thread start, which can not be translated into practice. There is also the problem of profile shift during screwing-in as a result of the not completely congruent tooth profile, whereby free play necessarily results between the thread tooth and the thread groove cut into the bone. The mentioned problems could explain why a socket of this type has not appeared commercially as a product.

Applicant's own calculations show that the stress of the bone ribs penetrating into the thread grooves of the socket has a very strong dependence upon the structural geometry. If one studies the main load bearing area approximately vertical above the implanted thread type socket, then it comes out that for the attainment of minimal forces and simultaneously a homogeneous force distribution a tilt angle of the thread ridge in the range of approximately 45° in the direction towards the socket pole is necessary, a value which no threaded hip joint socket commercially available today even comes close to satisfying. By increasing the tilting-back of the thread ridge into the neutral position (central axis of the thread ridge in the radial plane of the socket) the mathematical results of the model show an over-proportional increase of uneven load distribution of the involved bone material, wherein at the same time the stress values increase in their magnitude.

Further, an analysis of geometric conditions associated with the load transfer orthogonal to the main load bearing direction in an area of the threaded socket facing to the medial body direction proves that a tilting of the tooth profile in the direction to the socket pole has advantages associated with it. By this measure, namely, with increasing tilting angle, the portion of the shearing action of the complex load transfer upon the penetrating bone rib is reduced and in increasing measure replaced by more desirable bending forces or, as the case may be, by even more preferred compression forces.

In addition to these arguments, which from a purely medical point of view are vouching for the herewith proposed tilting of the thread profile, there results therewith at the same time also the advantage of simplified manufacture, since as a result thereof in the wedges close to the pole the angles between the equatorial side thread flank and the outer shell surface are not so acute. Therefore broader and therewith more sturdy cutting inserts are employable for the machining process.

The thread of the proposed type cannot simply be cut in a conventional manner, considering the necessary radial steps for a cutting sequence. In addition it has, when used with most threaded socket geometries, the important disadvantage, that it can not be screwed-in at all or will broadly destroy the bone-side tooth bed or, as the case may be, will require a high screw-in torque. These unacceptable disadvantages are necessarily associated with the conventional thread pitch, being constant in axial direction. This is the point of departure of the present invention, in which it is proposed that the pitch of the thread is varied along its course in a manner determined by the cutting force distribution, so that the above mentioned disadvantages are eliminated and the further above described advantages can be utilized.

For better understanding, the manner of determining the inventive special thread will now be discussed in individual steps. The first step is comprised therein, to arrange the individual teeth of the thread course in a semilateral axial section of the hip joint socket on the outer surface of the shell so that the projection centers of the respective tooth heads come to lie on linearly equidistant lines, that is, parallel lines in even separation to each other. In the case of very acute-angled threads the mentioned projection center lies thereby exactly upon the tooth head tip, while in the case of slender trapezoid shaped teeth it lies upon the intersection of the elongated flank lines. In a flat thread the center of the outer face of the thread tooth head is employed as the projection center. The individual lines of the so-formed set of lines shall be referred to as projection lines in the following. The initially angularly non-corrected projection lines run thereby as midlines or as angle bisectors of the respective thread tooth, in the axial sectional plane.

For the final angular establishment of these projection lines there is, in accordance with the invention, a correction angle introduced, of which the value is adaptable to produce the desired cutting force distribution between the two flanks of the thread ridge during the screwing-in process. The correction angle is limited to a maximum of half the angle enclosed between the two flanks, so that the corrected projection line, with the bandwidth of its positive or negative correction angle, is pivotable between the pole and the equator side tooth flanks about the projection center as center of rotation.

The cutting forces mentioned above are associated with the cutting-in process of the thread ridges during the screwing-in of the hip joint socket. They are composed of the actual cutting forces which are to be produced by the cutting edges of the thread ridges, the rasping forces based upon a roughened outer surface, and compression or, as the case may be, displacement forces, due to certain inaccessibilities of the thread arrangement and the yieldability of the involved bone region. It is thus desired, by means of an appropriately adjusted variation of the thread pitch, to reduce these complex cutting forces to a minimum, so that a soft and easy screwing-in of the implant is achievable even in harder bone structures.

The cutting edges mentioned above are produced in the threads of the artificial hip joint sockets by slitting the thread ridges, thus forming cutting grooves. A high number of slits and therewith cutting edges correspond to a lower specific cutting force load on the individual cutting edges. As a rule a generally reduced cutting force requirement is associated with this. The cutting force requirement is to be further influenced by the cutting angle, the sharpness of the cutting edge, and the so-called free angle.

In the true flat threads the actual cutting edge is formed on the tooth head. In this case, by means of an diagonally penetrating slitting a slightly positive cutting angle is realizable. Conventionally such flat threads are cut back by milling in the tooth head area behind the cutting edge, in order to achieve the desired free angle. The thread slitting then is generally relatively neutral, that is, essentially without twist. In this case the pure cutting forces are practically exclusively brought to bear on the head side of the thread tooth, while the flanks in the case of smooth surfaces are quasi non-participating. In the flanks there can however occur rasping forces, when the thread fins, for example by means of sand blasting, are made coarse. For this situation it is proposed to provide the conventionally parallel running tooth flanks of the flat thread with a very slight conical angle tapering towards the tooth head, in order to also guarantee a firm seat after the screwing-in. Even if rasping forces are transfered, depending upon the condition of the tooth flanks, these are in principle symmetrically balanced. Therefrom it follows that a correction angle for the projection line set, described in greater detail above, is not necessary. This is also valid for so-called triangular thread profiles and their modifications for the case of neutral running cutting grooves.

The situation for helical cutting grooves presents itself very differently since here the cutting forces are shifted to one of the two flanks of the thread ridge depending upon the helix direction. The degree of shifting depends therein upon the helix angle of the cutting groove. In the case of larger helix angles the cutting force then lies totally on one side. In order that, during the screwing-in process with such a threaded socket, the one-sided present cutting edge in the above described manner can actually develop its effect, it is necessary that the "pushing" of the tooth profile which occurs essentially in the radial direction be directionally influenced. In accordance with the invention, this occurs by applying the correction angle, mentioned above, during the determination of the corrected projection lines in such a manner that these are turned about its pivot point away from that tooth flank which is more strongly burdened with cutting force. It is proposed as advantageous in association therewith, that the degree of the correction is undertaken to be proportional to the relationship of the respective flank side total cutting forces, that is, the sum of the cutting, rasping and displacement forces.

For the rough determination of the variation of the thread pitch, the tilt angle of the thread tooth profile, the helix angle of the cutting grooves and the outer surface condition of the threaded socket to be manufactured must be known. On the basis of these data a roughly estimated determination of the force distribution acting upon the thread ridges during screwing-in is possible. For the achievement of an absolute minimum of the screw-in force requirement the carrying-out of screwing-in experiments on the basis of prototypes is recommended.

This procedure will now be described in the following on the basis of an example. Based on the assumption that the test model of a conventional threaded hip joint socket has a nominal diameter of 54 mm with a triangular thread (tooth height 2.5 mm, thread pitch 4 mm, thread extension 16 mm) in the machined condition, that is, with a relatively smooth surface, during screwing-in into a hard foam resin test body up to the seating of the shell jacket requires a maximum torque of 20 Nm, similarly one can with a second experiment find that the corresponding screwing-in torque for a sand-blasted version (coarseness $R_a$ for example 4 Mm) can for example be measured at 50 Nm. The portion of rasping forces from the total screwing-in torque then is with 30 Nm exactly 60%. These rasping forces are distributed evenly over the outer surface, and thus represent 30% per thread flank. In comparision the previously determined base torque in the amount of 20 Nm (corresponding to 40%) is comprised essentially of cutting forces, with a certain proportion of compression or, as the case may be displacement forces. In the case of a slanting of a cutting groove, when these cutting forces lie totally on one side of the flank of the thread tooth, the proportion of the total screwing-in torque on the flank provided with the cutting edge corresponds to 70%, so that the balance of 30% remains on the opposite side. If then the tilt angle of the center line of the thread tooth is 10° and the enclosed flank angle is 20°, then from the center line that corrected projection line is derived by placing the screwing-in force of 70% to 30% in relation-ship to the included flank angle. In a right-hand thread with a right-hand helix of the cutting groove the tilt angle of the projection line can be calculated therefrom at 14°.

After determining the line set of the corrected projection lines on the basis of the desired mean thread pitch, the tilt angle of the tooth profile and the desired cutting force distribution, the next step is comprised thereof, to determine upon the the selected shell geometry of the threaded socket (for example spherical, parabolical, etc.) the respective tooth height of the individual revolutions of the thread ridge and respectively the above mentioned projection point. Using this as a starting point the choosen side angles of the thread tooth profile are drawn up and their respective foot points on the shell outer surface are determined. These foot points are the basis for writing a machining program for the production of the inventive threads on a numeric controlled machine.

In general various processes for the production of special threads are known from patent literature, which in part can be adapted or modified insofar that they can be used for the production of the special threading first taught herein and the corresponding implants. In particular, in German Patent Application P 44 00 001.4 and its resulting International Application WO 95/18586, there are described different possibilities of processing a thread with a variable modifiable thread profile. These possess in their utilization various pitches, also a constantly varying value of the pitch, and the employment of varying offset values for the one or multiple machining tools, but these parameters are used in the quoted documents only for shaping the thread profile, thus leaving constant the actual thread pitch in axial direction. However, by applying this method it is also possible, in the maching cycle, to dive behind slanted thread ridges, to fit the thread bottom to the ideal contour with the highest possible resolution, and at the same time to realize with precision not only the tooth height, but also the respective tooth position according to the described teaching of the present invention. The manufacture by cutting using a CNC-lathe is particularly economical. With modern computer control systems of such machines there is, for example, in the command line G 33 a continous change of thread pitch directly programmable with E. Certain functions of the pitch change are achievable, for example, via the chain-linking of this type of command line or, as the case may be, the introduction of appropriate subprograms (for example by programming variables). For the person of ordinary skill in this art it poses no particular problem to write such CNC-programs specific for given machines.

BRIEF DESCRIPTION OF THE DRAWINGS

The invention will now be described in greater detail by reference to five figures.

DETAILED DESCRIPTION OF THE INVENTION

Figure 1:
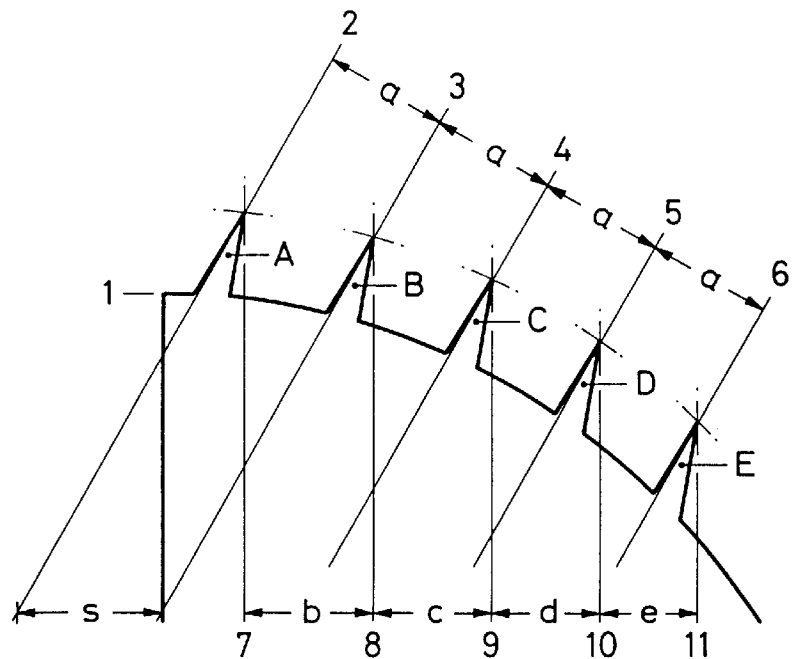
FIG. 1 shows a scheme for constructive determination of the course of the thread ridge using an example.

FIG. 1 illustrates the process steps for calculating the special thread in accordance with the invention by reference to an explanatory scheme. There is shown a contour 1 of a part of a circumference of a half side axial section of a threaded type socket, wherein for the example a spherical shell shape was selected. The revolving thread procession is sectionally represented by the individual teeth A, B, C, D and E, which are distributed in this series from the equatorial edge of the socket to the pole side cupola on the spherical shell mantle. The thread teeth are constructed in profile as sharp tipped triangles with their flanks including an angle of 22°. Further they are tilted at about 21° out of their neutral central position in a direction towards the socket pole. A set of straight, parallel and respectively by a value a equally distanced drawn lines 2, 3, 4, 5 and 6, the so-called corrected projection lines, were used in order to determine the positions of the individual thread teeth. The projection lines run within the angle defined by the flanks of the thread teeth, wherein their tilt angle was assumed to be 30°, since the example is based on strong right-hand slanted helical cutting grooves. The cutting grooves themselves are not visible in the illustration. They, because of their strong right-hand slant, achieve a formation of cutting edges which in the drawing would be right side, that is the pole side located flanks of the thread teeth. Thus, for achievement of a requirement-based function of this cutting edges, a stronger loading of the cutting forces on the pole side flank is to be desired. This is achieved in accordance with the invention by the angular turning away of the projection lines about the correction value, from which during screwing-in a corresponding "pushing" of the tooth cross-section in a certain working direction results. For the selected example, the surface of the threaded socket was provided, for example, with a fine roughening by sand blasting. Since from this a certain portion of rasping forces results on both sides of the thread tooth during screwing-in, the cutting force distribution between the tooth flanks was set at 9 to 91. In accordance with this example 91% of the cutting forces are to be produced by the pole side flank and 9% by the equatorial side flank of the thread tooth. Therefore the corrected projection line in the illustration figure is only offset with a 30° to perpendicular tilt angle, while the corresponding flank angle at 32° is 2° larger. The respectively indicated middle point crosses serve as a pivot point of the projection lines, which middle point crosses in the present case correspond with the respective thread tooth tips and result from the constructively choosen tooth height. The middle point crosses on the tooth tips are formed with the construction guide lines 7, 8, 9, 10 and 11 located perpendicularly to the socket axis, which on the basis of their axially measured distances b, c, d and e show the changes in the pitch measured at the tooth tips. For comparison the original pitch, s, was drawn-in as the horizontal separation of the projection lines. It should be noted that for the compilation of a suitable CNC machining program the thread pitch in the area of the foot-points of the thread teeth must be employed in synchrony with the corresponding reference point of the tool description.

Figure 2:
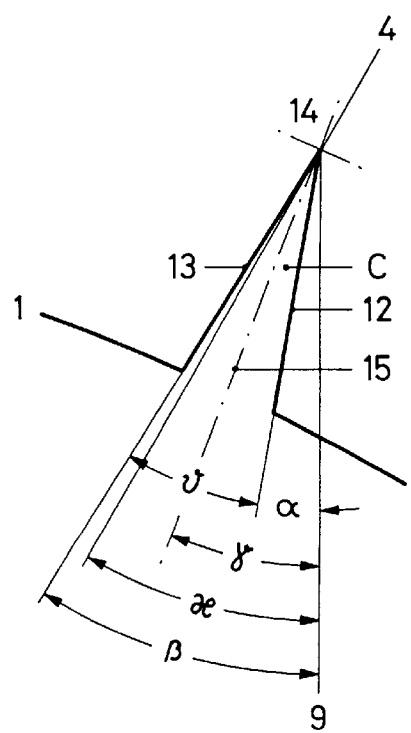
FIG. 2 shows the angular definitions on a thread tooth enlarged from the example according to FIG. 1.

For a better understanding of the situation represented in FIG. 1, and to give an overview representation of the various angles, the thread tooth C was taken and enlarged in FIG. 2. The contour course 1 is represented accordingly as a partial section. The pole side flank 12 of the thread tooth ist tilted away with an angle α of 10° right handed from the perpendicular construction guide line 9. The corresponding side angle β of the tooth flank 13 is 32°. Thus there results between the tooth flanks an enclosed angle δ of 22°. The dash-dot indicated angle bisector 15 is at the same time the uncorrected projection line which is pivotable about the pivot point 14 (here at the same time thread tooth tip). Its tilt angle is indicated with γ. The projection line 15 was corrected with an angle pivoted 9° towards the right, so forming the corrected projection line 4 with the pivot angle χ of 30°.

Figure 3:
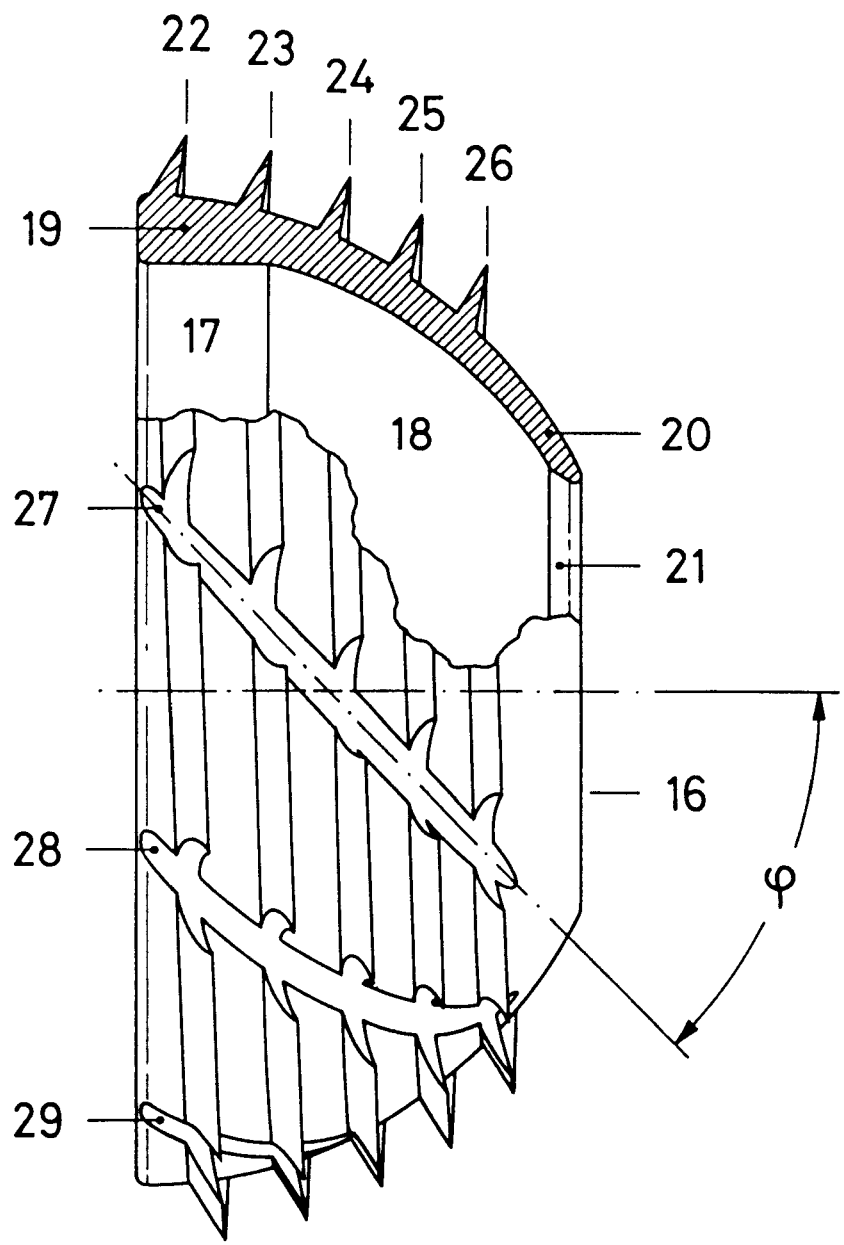
FIG. 3 shows an example of a hip joint socket according to the invention.

The example of a practical embodiment of the inventive hip joint socket is shown in FIG. 3. For this the thread design was followed the scheme of FIG. 1 and FIG. 2. The presented hemispheric hip joint socket 16 is partially cut away and drawn in section, in order to more clearly show the pattern of the wall and the threads. The inner design of the threaded socket is excavated in a cylindrical area 17 and a hollow spherical section 18 for the reception of a not shown inlay. The socket wall is designed to be thicker in the equatorial area 19, in order to machine-in grooves for the necessary screwing-in tool. Towards the socket cupola 20 the wall thickness becomes reduced. Adjacent thereto is a bottom hole 21, which makes possible a visual check of the socket seating during implantation. The indicated thread is constructed as a single thread. In the cross-section the disribution of the teeth 22, 23, 24, 25 and 26 of the thread procession along the shell mantle are recognizable. The teeth are clearly visibly tilted in a direction towards the socket pole. Along the thread procession, cutting grooves are formed by appropriate slitting with a radius miller, of which three (27, 28, and 29) are visible. The cutting grooves, relatively to the socket axis, are right-hand slanted with an angle φ, in order to form on the pole side flank cutting edges with a positive cutting angle.

Figure 4:
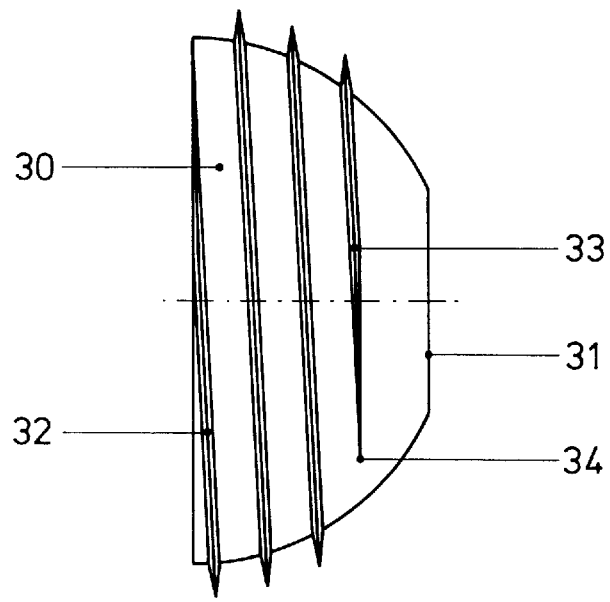
FIG. 4 schematically represents a conventional thread start of a hip joint socket, and FIG. 5 schematically represents a thread start according to the invention.

In the schematically simplified FIG. 4 a conventional hip joint socket with triangular threads is shown, wherein for example the perspective distortion of the thread is not taken into account. The threaded socket (30) has a hemispheric shell mantle. Because of the bottom hole, when viewed from the side a flattening (31) results. The thread profile is neutral, that is, without a tilt angle. The cutting grooves were omitted for reasons of simplification. The thread start (34) grows as the thread progresses up to transition point (33) to its full height. Then the thread ridge (32) revolves about three times up until the socket equator. Between the points 34 and 33, the flank of the thread tooth facing towards the socket pole exhibits no flank pitch. It is a relic of a conical annular surface, which results from the conventional pre-cutting process. As a result of the markedly skewing of this flank area relative to the thread progress, an unequal distribution of forces occurs upon the flanks in the screwing-in of the threaded socket. Thereby there results during screwing-in or, as the case may be, during pre-tapping with a tool, an unnecessary high force requirement.

Figure 5:
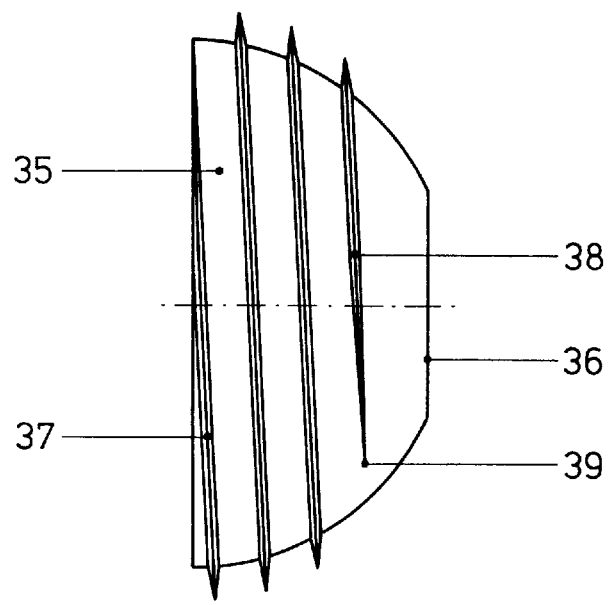

For comparison there is shown in FIG. 5 an example of a threaded socket with the inventive thread start. Fur porposes of better comparison the threaded socket (35) was reproduced without changes of the remaining details, so that the hemispheric shape, the flattening (36) and the thread ridge between points 38 and 37 of the threaded socket shown in FIG. 4 correspond. The portion from thread start (39) to transition point (38) was so slewed by shifting the thread start in the direction towards the socket pole that the forces acting upon the thread flanks are evened out. Therein the pole side tooth flank was cut with a smaller and the equator sided tooth flank with a larger, than the original pitch. With this design the screwing-in forces during implantation of the threaded socket or, as the case may be, the cutting forces during pre-tapping are markedly reduced in comparison with the conventional embodiments.

With the invention there is provided, all told, a threaded hip joint socket with a range of variations, which makes possible the employment of one or multiple start right or left-hand threads, neutral or right or, as the case may be, left-hand slanted cutting grooves and almost any tilt angle of the thread tooth profile with all possible shapes of the shell outer surface. Caused by the adaptability of the pitch variation in the thread procession to the respective type of construction and the possibility to specifically distribute the screwing-in forces on the thread ridges, there is for each embodiment the lowest possible screwing-in torque achievable, also with different degrees of outer surface coarseness. Thereby there is prevented not only a premature jamming of the threaded socket during screwing-in or, in certain cases, the risk of rupturing the pelvis, rather also in particular there is better tactile feedback of the seating position of the shell outer suface on the bone support. In the particularly preferred tilting of the thread teeth in the direction of the socket pole there is achieved in connection with the non-linear thread pitch a noticeable reduction of the load peaks during the conditions of use as directed of the implant. The inventive hip joint socket is, besides this, produceable in a problem-free manner and without additional costs, that is, on a CNC-lathe. Therewith the characteristics of the inventive threaded hip joint socket promise an advance in this area of medical technology.

What is claimed is:

1. Screw-in type artificial hip joint socket comprising a shell body having an outer surface, said outer surface having a threaded portion provided thereon with a self-tapping threading for screwing into the acetabulum along a socket axis, said outer surface exhibiting a progressive or stepwise resolved curvature within said threaded portion, said threading having helical cutting grooves and/or a thread tooth profile tilted away from a plane radial to said socket screw-in axis, wherein said the thread has a pitch that varies relative to said socket axis depending upon:

(a) the curvature of the shell body outer contour relative to said socket axis, (b) the angle of tilt of the thread tooth profile, (c) the twist angle of the cutting groove, and (d) the coarseness of the texture of the thread surface.

2. Screw-in type artificial hip joint socket according to claim 1, said socket having an equator side and a pole side, wherein the thread in the pole side starting portion between the initial surfacing (39) of the thread tooth and the achievement of a full tooth height (38) is provided with a pitch of the pole side thread tooth flank which is smaller, and a pitch of the equator side thread tooth flank which is larger than the original pitch of the socket thread.

3. Screw-in type artificial hip joint socket according to claim 1, wherein the thread tooth profile is tilted with an angle (γ) out of the radial plane, and either no cutting grooves are provided within the thread or, if cutting grooves are provided, these run with a helix angle of zero, wherein the thread teeth of the thread distributed in a corresponding half side axial section of the hip joint socket are placed with their respective midlines (15) on equidistants, thus parallel and in the same distance to each other running lines.

4. Screw-in type artificial hip joint socket according to claim 1, wherein the self-tapping thread is provided with flat threads for cementless anchoring in the acetabulum with radially effective cutting edges outlying on the tooth head, and the thread ridge procession formed upon the shell mantle at least is partially structured or roughened, and in order to compensate the rasping effect of the thread tooth flanks these run in direction to the tooth head with an angle between 0.5 and 5° measured flank to flank towards each other.

5. Screw-in type artificial hip joint socket according to claim 1, wherein the threading is provided with a tooth profile narrowing towards the tooth head at any angle and with helical cutting grooves (27, 28, 29), wherein the thread teeth (A, B, C, D, E) of the thread distributed upon the shell mantle in the half side axial section of the hip joint socket are placed with the point of intersection (14) of their side lines (12, 13) joining the thread tooth flanks upon equidistant corrected projection lines (2, 3, 4, 5, 6), thus parallel and respectively with the same distance to each other running lines, of which the angular position is determined between the two flanks (12, 13) of the thread tooth, using the point of intersection (14) of the side lines joining the thread tooth flanks as the angular rotation point.

6. Screw-in type artificial hip joint socket according to claim 5, wherein the corrected projection lines are slewed away from the midline (15) in the direction toward the thread tooth flank less burdened with cutting forces.

7. Screw-in type artificial hip joint socket according to claim 6, wherein the degree of the angular rotation of the corrected projection lines is proportional to the relationship of the cutting forces to be acting on the thread tooth flanks, and the angle γ of the corrected projection lines (2, 3, 4, 5, 6) is described essentially by the equation:

$$\text{Angle } x = \text{Angle } \alpha + \frac{\text{Angle } \delta \cdot \text{Force } F_{PA}(\%)}{100},$$

where

χ=angle of the corrected projection lines (in degrees)

α=pole side thread tooth side angle (in degrees)

δ=enclosed thread tooth flank angle (in degrees)

$F_{PA}$=desired percentile pole side portion of the totally acting complex forces upon both thread tooth flanks, composed of cutting-, rasping-, and compressing or, as the case may be, displacement forces.

8. Screw-in type artificial hip joint socket according to claim 1, wherein the threading is provided with a thread tooth profile narrowing towards the tooth head at any angle and tilted with an angle (γ) out of the radial plane, the threading having helical cutting grooves (27, 28, 29), wherein the thread teeth (22, 23, 24, 25, 26) distributed upon the shell mantle in the half side axial section of the hip joint socket are placed with the point of intersection (14) of their side lines joining the tooth flanks upon equidistant corrected projection lines (2, 3, 4, 5, 6), thus parallel and respectively with the same distance to each other running lines, of which the angular position is determined between the two flanks (12, 13) of the thread tooth, wherein the point of intersection (14) of their joining side lines is used as the angular rotation point.

9. Screw-in type artificial hip joint socket according to claim 8, wherein the corrected projection lines are slewed away from the midline (15) in the direction toward the thread tooth flank less burdened with cutting forces.

10. Screw-in type artificial hip joint socket according to claim 9, wherein the degree of the angular rotation of the corrected projection lines is proportional to the relationship of the cutting forces to be acting on the thread tooth flanks, and the angle γ of the corrected projection lines (2, 3, 4, 5, 6) is described essentially by the equation:

$$\text{Angle } x = \text{Angle } \alpha + \frac{\text{Angle } \delta \cdot \text{Force } F_{PA}(\%)}{100},$$

where

χ=angle of the corrected projection lines (in degrees)

α=pole side thread tooth side angle (in degrees)

δ=enclosed thread tooth flank angle (in degrees)

$F_{PA}$=desired percentile pole side portion of the totally acting complex forces upon both thread tooth flanks, composed of cutting-, rasping-, and compressing or, as the case may be, displacement forces.

11. Screw-in type artificial hip joint socket according to claim 1, wherein the threading is provided with a thread tooth profile with parallel flanks tilted with an angle (γ) out of the radial plane, the threading having helical cutting grooves, wherein the thread teeth distributed upon the shell mantle in the half side axial section of the hip joint socket are placed upon equidistant corrected projection lines (2, 3, 4, 5, 6), thus parallel and respectively with the same distance to each other running lines, of which the angular position is determined between the two thread tooth flanks, wherein the center of the thread tooth head is used as the angular rotation point.

12. Screw-in type artificial hip joint socket according to claim 9, wherein the corrected projection lines are slewed away from the midline (15) in the direction toward the thread tooth flank less burdened with cutting forces.

13. Screw-in type artificial hip joint socket according to claim 11, wherein the degree of the angular rotation of the corrected projection lines is proportional to the relationship of the cutting forces to be acting on the thread tooth flanks, and the angle χ of the corrected projection lines (2, 3, 4, 5, 6) is described essentially by the equation:

$$\text{Angle } x = \text{Angle } \alpha + \frac{\text{Angle } \delta \cdot \text{Force } F_{PA}(\%)}{100},$$

where

χ=angle of the corrected projection lines (in degrees)

α=pole side thread tooth side angle (in degrees)

δ=enclosed thread tooth flank angle (in degrees)

$F_{PA}$=desired percentile pole side portion of the totally acting complex forces upon both thread tooth flanks, composed of cutting-, rasping-, and compressing or, as the case may be, displacement forces.

14. Screw-in type artificial hip joint socket according to claim 1, wherein the thread tooth profile is tilted in the direction to the socket pole in slewing the pole side flank (12) of the thread tooth (C) with an angle (α) beyond the radial plane in the direction to the socket pole.

* * * * *

UNITED STATES PATENT AND TRADEMARK OFFICE
CERTIFICATE OF CORRECTION

PATENT NO. : 6,146,425
DATED : November 14, 2000
INVENTOR(S) : Gerd Hoermansdoerfer It is certified that error appears in the above-identified patent and that said Letters Patent is hereby corrected as shown below:

Column 10,
Line 9, cancel beginning with "1. Screw-in" to and including "thread surface."
Line 24, and insert the following claim:

1. Screw-in type artificial hip joint socket comprising a shell body having an outer surface, said outer surface having a threaded portion provided thereon with a self-tapping threading for screwing into the acetabulum along a socket axis, said outer surface exhibiting a progressively or stepwise resolved curvature within said threaded portion, said threading having twisted tapping grooves and/or a thread tooth profile tilted away from a plane radial to said socket screw-in axis, wherein said thread has a pitch that varies relative to said socket axis depending upon:
    (a) the curvature of the shell body outer contour relative to said socket axis,
    (b) the angle of tilt of the thread tooth profile,
    (c) the twist angle of the tapping groove, and
    (d) the roughness of the thread surface.

Line 42, cancel beginning with "4. Screw-in" to and including "each other."
Line 51, and insert the following claim:

4. Screw-in type artificial hip joint socket according to claim 1, wherein the self-tapping thread is provided with radially effective cutting edges outlying on the tooth head as in the conventional flat threads for cementless anchoring in the acetabulum, and the thread ridge procession formed upon the shell mantle at least is partially structured or roughened, and in order to compensate the rasping effect of the thread tooth flanks these run in direction to the tooth head with an enclosed angle between 0.5 and 5° measured flank to flank towards each other.

Column 11,
Line 3, cancel begininng with "7. Screw-in" to and including "displacement forces."
Line 22, and insert the following claim:

7. Screw-in type artificial hip joint socket according to claim 6, wherein the degree of the angular rotation of the corrected projection lines is proportional to the relationship of the cutting forces to be acting on the thread tooth flanks, and the angle $\chi$ of the corrected projection lines (2, 3, 4, 5, 6) is described essentially by the equation:

UNITED STATES PATENT AND TRADEMARK OFFICE
CERTIFICATE OF CORRECTION

PATENT NO. : 6,146,425
DATED : November 14, 2000
INVENTOR(S) : Gerd Hoermansdoerfer It is certified that error appears in the above-identified patent and that said Letters Patent is hereby corrected as shown below:

$$\text{Angle } \chi = \text{Angle } \alpha + \frac{\text{Angle } \delta \cdot \text{Force } F_{PA}(\%)}{100},$$

where
$\chi$ = angle of the corrected projection lines (in degrees).
$\alpha$ = pole side thread tooth side angle (in degrees)
$\delta$ = enclosed thread tooth flank angle (in degrees)
$F_{PA}$ = desired percentile pole side portion of the totally acting complex forces upon both thread tooth flanks, composed of cutting-, rasping-, and compressing or, as the case may be, displacement forces.
Line 42, cancel beginning with "10. Screw-in" to and including "displacement forces."

Column 12,
Line 9, and insert the following claim:

10. Screw-in type artificial hip joint socket according to claim 9, wherein the degree of the angular rotation of the corrected projection lines is proportional to the relationship of the cutting forces to be acting on the thread tooth flanks, and the angle $\chi$ of the corrected projection lines (2, 3, 4, 5, 6) is described essentially by the equation:

UNITED STATES PATENT AND TRADEMARK OFFICE
CERTIFICATE OF CORRECTION

PATENT NO. : 6,146,425
DATED : November 14, 2000
INVENTOR(S) : Gerd Hoermansdoerfer It is certified that error appears in the above-identified patent and that said Letters Patent is hereby corrected as shown below:

$$\text{Angle } \chi = \text{Angle } \alpha + \frac{\text{Angle } \delta \cdot \text{Force } F_{PA} (\%)}{100},$$

where
$\chi$ = angle of the corrected projection lines (in degrees)
$\alpha$ = pole side thread tooth side angle (in degrees)
$\delta$ = enclosed thread tooth flank angle (in degrees)
$F_{PA}$ = desired percentile pole side portion of the totally acting complex forces upon both thread tooth flanks, composed of cutting-, rasping-, and compressing or, as the case may be, displacement forces.

Signed and Sealed this

Thirteenth Day of November, 2001

*Attest:*

Nicholas P. Godici

NICHOLAS P. GODICI
*Attesting Officer*     *Acting Director of the United States Patent and Trademark Office*